(12) United States Patent
Smith et al.

(10) Patent No.: US 6,980,419 B2
(45) Date of Patent: Dec. 27, 2005

(54) PORTABLE ULTRASOUND UNIT AND DOCKING STATION

(75) Inventors: Scott F. Smith, Oak Creek, WI (US); Michael E. Hayden, Saratoga, CA (US); Ian Felix, Los Gatos, CA (US); Derek DeBusschere, Orinda, CA (US); Glen McLaughlin, Saratoga, CA (US)

(73) Assignee: ZONARE Medical Systems, Inc., Mountain View, CA (US)

( * ) Notice: Subject to any disclaimer, the term of this patent is extended or adjusted under 35 U.S.C. 154(b) by 0 days.

(21) Appl. No.: 10/389,356

(22) Filed: Mar. 12, 2003

(65) Prior Publication Data

US 2004/0179332 A1    Sep. 16, 2004

(51) Int. Cl.[7] ................................................. G06F 1/16
(52) U.S. Cl. ........................................ 361/681; 361/679
(58) Field of Search .................................. 361/679, 681

(56) References Cited

U.S. PATENT DOCUMENTS

| | | | |
|---|---|---|---|
| 3,951,140 A * | 4/1976 | Eggleton et al. | 600/439 |
| 5,590,658 A | 1/1997 | Chiang et al. | |
| 5,690,114 A | 11/1997 | Chiang et al. | |
| 5,722,412 A * | 3/1998 | Pflugrath et al. | 600/459 |
| 5,839,442 A | 11/1998 | Chiang et al. | |
| 5,957,846 A | 9/1999 | Chiang et al. | |
| 5,964,709 A | 10/1999 | Chiang et al. | |
| 6,106,472 A | 8/2000 | Chiang et al. | |
| 6,126,608 A | 10/2000 | Kemme et al. | |
| 6,135,961 A | 10/2000 | Pflugrath et al. | |
| 6,203,498 B1 | 3/2001 | Bunce et al. | |
| 6,447,451 B1 * | 9/2002 | Wing et al. | 600/437 |
| 6,471,651 B1 | 10/2002 | Hwang et al. | |
| 6,497,661 B1 | 12/2002 | Brock-Fisher | |
| 6,524,244 B1 | 2/2003 | Knell et al. | |
| 6,527,721 B1 | 3/2003 | Wittrock et al. | |
| 6,542,846 B1 * | 4/2003 | Miller et al. | 702/132 |
| 6,569,101 B2 * | 5/2003 | Quistgaard et al. | 600/459 |
| 6,575,906 B1 * | 6/2003 | Schembri et al. | 600/437 |
| 6,575,908 B2 * | 6/2003 | Barnes et al. | 600/443 |
| 2002/0007119 A1 | 1/2002 | Pelisser | |
| 2002/0173721 A1 * | 11/2002 | Grunwald et al. | |

* cited by examiner

Primary Examiner—Yean-Hsi Chang
(74) Attorney, Agent, or Firm—Fish & Neave IP Group Ropes & Gray LLP; Norman H. Beamer; Chi-Hsin Chang

(57) ABSTRACT

A portable ultrasound unit and docking cart for the unit are provided. When the portable unit is mounted to the docking cart, the docking cart transforms the portable unit into a cart-based system with enhanced features and functionality such as improved ergonomics, ease of use, a larger display format, external communications connectivity, multiple transducer connections, and increased data processing capabilities. A clinician display and patient display may be provided on the cart. Communications circuitry in the docking cart may be used to support communications between the docking cart's processor and external networks and devices. The docking cart may receive physiological signals such as cardiac signals and may use this information to synchronize ultrasound imaging operations with a patient's physiological condition. Adjustable user interface controls, data handling features, security features, power control functions, and thermal management capabilities may be provided in the docking cart.

36 Claims, 8 Drawing Sheets

PORTABLE ULTRASOUND UNIT AND DOCKING STATION

BACKGROUND OF THE INVENTION

This invention relates to ultrasound equipment, and more particularly, to portable ultrasound units and docking stations for such units.

Ultrasound equipment is used in a variety of medical applications. Small hand-held ultrasound scanners are used for applications in which portability is at a premium. Such scanners, while portable, are not as full-featured as larger equipment. Accordingly, there remains a need for full-sized cart-based ultrasound scanners. Such cart-based ultrasound scanners, which typically weigh hundreds of pounds, have more capabilities than small portable units. These traditional cart-based scanners can be moved between different rooms in a medical establishment, but are not portable.

What is needed is a way in which to benefit from the advantageous qualities of both portable ultrasound units and more full-featured equipment.

SUMMARY OF THE INVENTION

In accordance with the present invention, a portable ultrasound unit and associated docking cart are provided. The portable ultrasound unit may be small enough to be carried in the hands of a medical professional or other user. When appropriate, the portable ultrasound unit may be used in conjunction with the docking cart. The docking cart may enhance the capabilities of the portable unit so that the portable unit's functionality rivals or exceeds the capabilities of traditional cart-based ultrasound equipment.

If desired, the portable ultrasound unit may be mounted to the docking cart. Electrical and physical connections may be used when mating the portable ultrasound unit to the docking cart.

With one suitable physical mounting arrangement, the docking cart has a receptacle into which the portable unit may be placed. This arrangement allows a user of the ultrasound equipment to secure the portable device to the docking cart during use.

Electrical connections between the docking cart and the portable ultrasound unit allow power and data signals to be shared. For example, image data from the portable ultrasound unit may be transmitted to the docking cart and control data and power may be provided from the docking cart to the portable unit.

The portable ultrasound unit and docking cart may communicate using digital communications. For example, image data and other data may be transferred between the portable ultrasound unit and the docking cart over a high-speed digital communications link.

The docking cart's processing capabilities may be used to process image data provided to the cart by the portable ultrasound unit. Image data for the portable unit may be provided to the cart in a relatively unprocessed condition, thereby allowing the docking cart to provide enhanced processing capabilities before potentially useful information in the image data has been lost through the processing steps performed by the portable scanner. The enhanced processing capabilities of the cart may be provided through the use of a processor such as a processor based on an embedded control system on the cart. If desired, image data may be provided to the cart in a relatively processed condition to ease the processing burdens on the docking cart processor.

The portable ultrasound unit and docking cart may have displays for displaying ultrasound images and other information to clinicians and patients. The display format used by the portable unit's display may be different than the display format used by the docking cart's display. With this type of arrangement, ultrasound images may be displayed in higher resolution on the docking cart's display than on the portable unit's display.

An articulating arm may be used to support one or more of the cart's displays. The displays may include a patient monitor that may be easily positioned for viewing by the patient. User displays such as the primary display intended for viewing by the clinician may include medical annotations. Some or all of this annotation information and other potentially sensitive information may be suppressed when displaying images for the patient on the patient monitor.

The display on the portable ultrasound unit may be relatively small, to maintain the portability of the portable unit, whereas the display on the docking cart may be larger, as it is not faced with these same size constraints. The cart may have connectors that allow the connection of additional display peripherals. The displays on the cart may be controlled by the cart's processor.

Communications between the docking cart and portable ultrasound unit may be supported using one or more unidirectional links or bidirectional links. Multiple links may be operated in parallel to enhance throughput. Serial links may be used to reduce the number of signal lines used to handle the data. The communications links between the docking cart and portable ultrasound unit may be used to convey data from the portable unit to the docking cart.

Digital control data from the docking cart may be transmitted to the portable ultrasound unit, thereby allowing user controls on the docking cart to be used to control the functions of the portable unit. The docking cart may have more room for controls than the relatively small portable ultrasound unit. If desired, the docking cart may have controls such as knobs, sliders (e.g., for depth-gain compensation adjustments), buttons, a touch-screen with soft menu options, keyboard keys, a trackball, a touch pad, or other suitable user interface devices. These controls may be used to supplement or override the controls that are available on the portable ultrasound unit. The controls may be laid out in a fashion that simulates the control layout of traditional cart-based ultrasound systems.

The controls on the cart may be provided on a control panel. The control panel may be mounted to the cart using a mounting arm or other arrangement that allows the position of the control panel to be adjusted relative to the rest of the cart. For example, the height of the control panel and the angle or tilt of the control panel relative to the cart may be adjusted.

The cart may have wheels. The wheels may swivel independently to allow the cart to be easily moved. A foot switch or other control may be used to lock the wheels to prevent undesired movement. The wheels may be automatically locked using processor-controlled actuators (e.g., to prevent the cart from being removed without authorization). Both the swiveling action of the wheels and the wheels' rotation can be locked.

The docking cart may have an internal battery that can be used to extend the amount of time that the portable ultrasound device can operate from battery power. The docking cart may also have external battery charging receptacles that can be used to recharge and condition the batteries used by the portable ultrasound unit and other medical equipment.

Ultrasound readings may be taken of a medical patient or other image target using a variety of ultrasound transducers. The portable ultrasound unit may have a transducer port to which a desired cabled transducer head may be connected. A user of the portable unit may swap a new transducer into place by changing which transducer is connected to the transducer port.

The mounting arrangement used to attach the portable ultrasound device to the docking cart may provide sufficient room to allow the transducer head to remain connected to portable unit, even after the portable unit is attached. This type of arrangement may be used to allow this ultrasound transducer to be used to acquire images from the image target, while the portable ultrasound unit is connected to the docking cart. Different transducers may also be swapped into place while the unit is in the docking cart.

If desired, the docking cart may have transducer expansion ports. These expansion ports may be used to connect ultrasound transducer heads to the cart. The cart may have multiplexing circuitry that may be used to select which of the ultrasound transducer heads connected to the expansion ports is active. Signals from the expansion port transducer may be routed through the analog-front-end electronics of the portable ultrasound unit, so that this processing circuitry does not need to be duplicated on the docking cart.

The cart processor is not limited by the same size and power supply constraints faced by processors in portable ultrasound units. Accordingly, the cart processor may be more powerful and flexible in some respects than the portable unit's processor. The enhanced processing capabilities of the cart may be used to supplement or replace processing that would otherwise be performed by the portable unit. For example, the cart processor may be used to provide three-dimensional image rendering capabilities that are beyond the processing capabilities of the portable ultrasound unit operating alone. As another example, the cart processor may be used to provide access to powerful data processing ("Calc") packages or access to large databases. The cart processor may, for example, maintain a large ultrasound image database. The cart processor may be used to compare images from the portable unit with images in the cart's image database. The images from the portable unit may be acquired while the portable unit is docked or the images may be downloaded to the cart after they have been acquired by an undocked portable unit.

If desired, the user of the portable unit may download images from the unit to storage in the cart for archiving on the docking cart or a network connected to the docking cart (e.g., a hospital's computer network). By using the cart's processor to make comparisons between recently-acquired images and archived images from a given patient, a clinician can track changes in the patient's condition to detect important trends. The clinician may also use the cart processor and imaging database capabilities of the cart to compare a patient's images to images of other patients or standard images in the image database.

The docking cart may have internal digital storage such as memory chips or a hard drive for supporting image database storage needs and other data storage functions. The docking cart may also have one or more removable media drives (e.g., recordable DVD drives, compact flash slots or other suitable memory card readers, etc.).

To acquire high-quality ultrasound images, an impedance-matching gel may be applied between the ultrasound transducer (scanner head) and the patient's skin. The docking cart may have a heating arrangement for heating the gel to a temperature that makes application of the gel to the patient comfortable.

The docking cart may have ports for connecting peripherals to the cart. Peripheral devices that may be connected to the docking cart include printers, monitors, video-cassette recorders, and external storage devices (e.g., external DVD drives, magneto-optical drives, or hard drives).

The docking cart may also have ports for connecting external physiological sensors or other medical equipment. Sensors that may be connected to the docking cart include EKG devices, respiration measurement devices, blood oxygen sensors, pulse monitors, etc. Signals associated with these sensors may be processed externally or may be processed using the processing capabilities of the docking cart. The physiological inputs from the physiological sensors may be used to as a trigger signal when performing ultrasound scans.

Communications ports may be provided on the docking cart that allow the docking cart to communicate with external devices and networks. The communications ports may, for example, include Ethernet ports, wireless ports, USB ports, or any other suitable wired or wireless communications ports.

The docking cart may have microphone inputs for receiving voice annotations from clinicians and for making audio measurements (e.g., in conjunction with ultrasound image acquisition). The docking cart may have speakers for providing audio feedback to the user (e.g., for playing back the patient sounds acquired from a microphone in real time).

The docking cart may have a locking latch or other locking mechanism that may be used to secure the portable ultrasound unit into place in the cart to prevent theft. A metal loop may be provided on the cart to allow the cart to be locked to a stationary object using a cable or chain.

The processor may communicate regularly with a communications network. When the processor detects that the cart has been unexpectedly disconnected from the network or moved to an unauthorized location, the processor may turn off some or all of the cart's functions to prevent unauthorized use of the cart. In this type of situation, the processor may also lock the wheels of the cart or use electronic communications (e.g., email) to send an alert indicating that the cart may have been misappropriated.

The normal thermal regulating mechanisms of the portable ultrasound unit may be supplemented by the cart. For example, the docking cart may provide a heatsink surface that helps to dissipate heat generated by the portable ultrasound unit when the unit is mounted to the cart. The docking cart may also use a supplemental fan, Peltier-effect cooler, or air channels to help remove heat from the portable ultrasound unit when it is mated to the cart.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
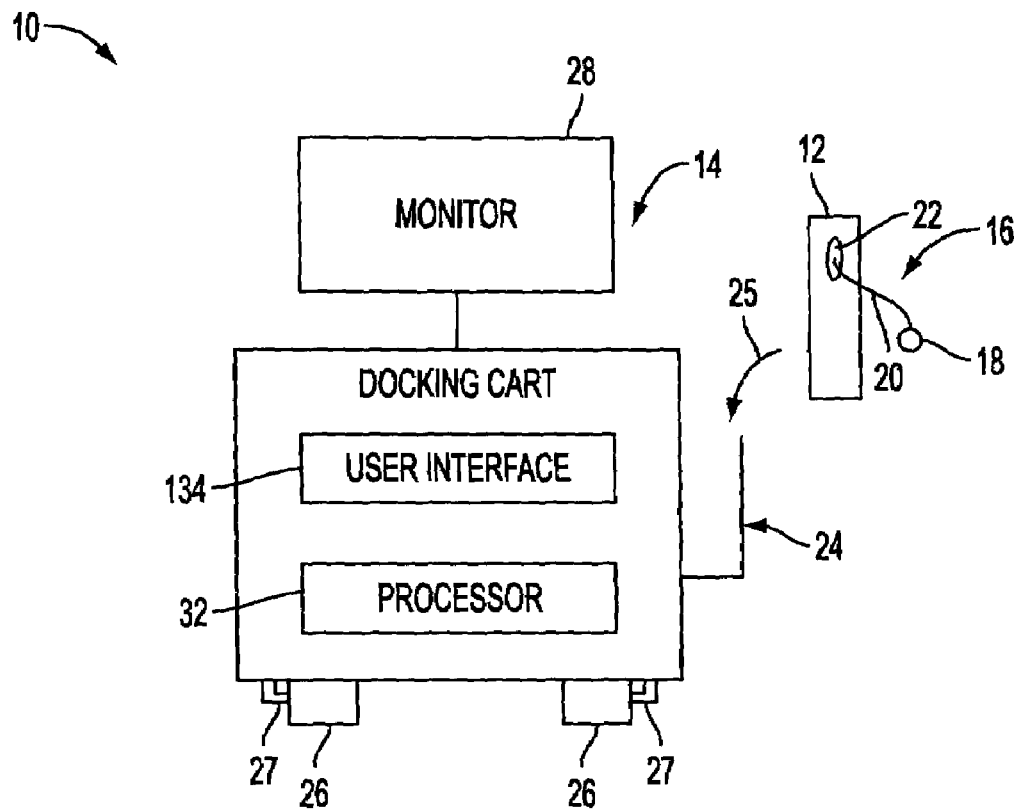
FIG. 1 is a schematic diagram of an illustrative portable ultrasound unit and docking cart in accordance with the present invention.

An illustrative portable ultrasound unit 12 and docking cart 14 in a system 10 in accordance with the present invention are shown in FIG. 1. The portable ultrasound unit 12 may be small and light enough to be easily carried by a user (e.g., a physician or other clinician in a medical setting or other suitable individual). The unit may, if desired, be small and lightweight enough to be carried in a single outstretched arm.

Standard cart-based ultrasound equipment generally weighs hundreds of pounds and is either stationary or is movable only with considerable effort. Accordingly, portable ultrasound units such as unit 12 may often be much more appropriate to use than traditional cart-based ultrasound systems. For example, portable ultrasound unit 12 may be used when ultrasound capabilities are needed in the field (e.g., in an ambulance) or even in a clinical setting such as a hospital in which the ability to easily transport the unit 12 from location to location is important. The weight of the portable unit 10 may be on the order of 5 or 10 pounds or less or may be any other suitable weight. The size of the portable unit 12 may be on the order of 4 inches×10 inches by 12 inches or any other suitable size. These are merely illustrative weights and dimensions. Portable unit 12 may have any suitable size and weight if desired.

Ultrasound images may be gathered using ultrasound transducer 16. Transducer 16 may have a transducer head 18 and may be connected to portable unit 12 using a cable 20 and connector 22 or other suitable interconnection arrangement. Different transducers may be used for making different types of ultrasound measurements. For example, medium frequency transducers with phased arrays may be particularly useful for applications in cardiology or abdominal imaging. High-frequency linear transducers may be used for muscular work. Curvilinear transducer heads may be preferred when making abdominal measurements. Probe-based and catheter-based ultrasonic transducers may also be used with portable unit 12 if desired. To allow different transducers to be used, portable ultrasound unit 12 may have a transducer port to which different transducer connectors 22 may be attached, as needed.

Docking cart 14 may have a docking structure 24 that allows portable unit 12 to be connected to docking cart 14. The docking structure 24 may be a shelf, receptacle, drawer, slot, recess, clasp, mating protrusion, or any other docking structure that facilitates attachment of portable unit 12 to docking cart 14. In the example of FIG. 1, docking structure 24 is a vertically-loaded receptacle into which portable ultrasound unit 12 may be inserted as shown by arrow 25. This is, however, merely one suitable arrangement for docking structure 24. Docking structure 24 may have a different configuration if desired.

Structure 24 may be used to physically secure unit 12 to cart 14. Electrical connections between portable ultrasound unit 12 and docking cart 14 may also be made to allow information to be shared between cart 14 and unit 12.

Cart 14 is preferably substantially larger than portable unit 12. For example, cart 14 may be large enough to be pushed about on its wheels 26 by a standing user, without requiring that the user stoop or bend over excessively. Smaller or larger carts 14 may be provided if desired. Because cart 14 has wheels 26, the weight of cart 14 may be considerably greater than that of portable unit 12. Each wheel 26 may be a swivel wheel that can be independently locked to prevent swivel movement, allowing the cart to be pushed down a corridor in a straight line. Wheels can also be locked to prevent rotation (e.g., to prevent cart 14 from being stolen). The rotational or swivel motion of wheels 26 may, if desired, be locked in unison (e.g., using a system of cables to mechanically actuate locks 27 together or by using electromagnetically-actuated locks 27). Cart 14 may have any suitable number of wheels 26 (e.g., 3–8 wheels).

Because cart 14 is larger than unit 12 and may weigh more than unit 12, cart 14 may have features that can be used to supplement the capabilities of unit 12. When the portable unit is mounted to the docking cart, the docking cart in effect transforms the portable unit into a cart-based system with enhanced features and functionality. These enhanced capabilities may include improved ergonomics, ease of use, a larger display format, external communications connectivity, supplemental transducer ports, and increased data processing capabilities.

Cart 14 may have one or more supplemental displays such as monitor 28 that may be used to enhance or replace the display capabilities of the portable ultrasound unit 12. Docking cart 14 may also have a user interface 134 and processor 32 that may be used to supplement or replace the user interface and processing capabilities of unit 12. For example, user interface 134 may include a full-size keyboard for data entry, which may be easier to use than the data entry arrangement of the portable unit 12. As another example, processor 32 may have more storage and greater or more flexible processing capabilities than the processor circuitry in unit 12.

The enhanced processing capabilities of cart 14 may be used to provide features that would otherwise be difficult or impossible to implement using only portable unit 14. For example, the cart processor may be used to provide three-dimensional image rendering capabilities that are beyond the processing capabilities of the portable ultrasound unit operating alone. The cart's processor may also be used to implement powerful data processing packages. Large databases of ultrasound images or other patient data or reference-type medical data may be maintained by the cart's processor and associated storage devices. The cart's processor may help to coordinate access to network-based resources (e.g., medical data maintained on a hospital network).

A user may download patient data such as ultrasound image data or other data from the portable unit 14 to the cart 12. The downloaded data may be stored on the cart (e.g., in an image database or archive implemented using a hard drive) or may be stored on a network connected to the cart. The cart processor may be used to compare recently-gathered patient images from the portable unit with historical images of the same patient or with other patient images that are maintained in the cart's image database.

The images may be obtained from the portable unit in real time while the portable unit is docked or may be downloaded from the unit at some time after the images are acquired. By using the cart's processor to make comparisons between a patient's current images and that patient's archived images, a clinician can track changes in the patient's medical condition and thereby detect trends in the patient's condition. The clinician may also use the cart processor and imaging database capabilities of the cart to compare a patient's images to images of other patients or standard images in the image database.

Figure 2:
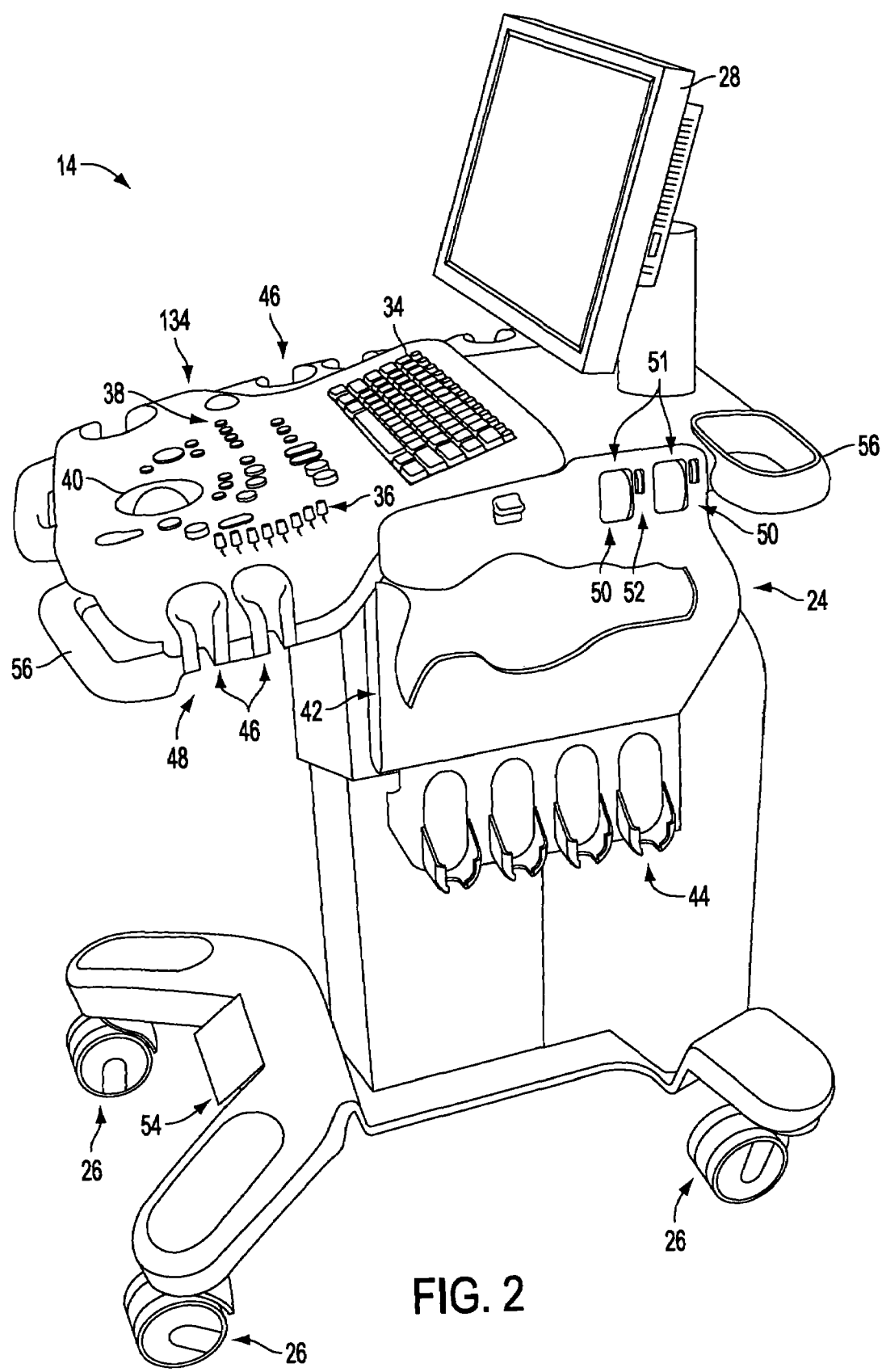
FIG. 2 is a perspective view of an illustrative docking cart in accordance with the present invention.

An illustrative docking cart 14 is shown in FIG. 2. In the illustrative example of FIG. 2, docking cart 14 has a large high-resolution monitor 28 such as a 18" color LCD flat panel display. Monitor 28 may be any suitable size, but a larger monitor (e.g., 18" diagonally or more) may be preferable in some working environments, because it presents a larger easier-to-view image for the user.

Docking cart 14 of FIG. 2 has a user interface 134 that includes a full-size keyboard 34, sliders 36 (e.g., for control of depth-gain compensation), various knobs and buttons 38, and a trackball 40. Other suitable user interface devices include touch pads, touch screens, voice recognition and audio equipment, a computer mouse, a joystick or other pointing device, etc.

Cart 14 has a docking structure or receptacle 24 into which portable ultrasound unit 12 (FIG. 1) may be inserted. Receptacle 24 may have a cutout portion 42 that allows the transducer connector 22 and associated cable 20 of the transducer to protrude out of the portable ultrasound unit 12 while the unit 12 is attached to cart 14. The transducer head 18 of the transducer attached to the portable unit 12 and the transducer heads of additional transducers 16 may be placed in transducer holders 44 or one of the additional holders 46 on the main control panel portion 48 of the docking cart. Holders such as holders 46 may be used for any desired purpose such as for holding ultrasound gel, tissues, transducers or other medical instruments, etc.

The portable ultrasound unit 12 and other devices used by the user may be powered (at least some of the time) using batteries. Cart 14 may have integral battery charging ports 51. As shown in FIG. 2, batteries 50 may be charged and conditioned in these receptacles. If desired, the battery ports may each have an accompanying battery release mechanism activated by a button 52. The battery charging ports 51 may be used to recharge depleted batteries, may be used to recondition batteries in need of reconditioning, and may serve as a convenient storage location for charged fresh batteries.

Docking cart 14 may have wheels such as lockable swivel wheels 26 of FIG. 2 or any other suitable wheels or mechanisms for facilitating movement of docking cart 14. Wheels 26 may be locked by depressing foot pedal 54 (which may be connected to one or more of wheels 26 by internal cabling) or by using other manually-controlled or electronically-controlled electromechanical actuators such as locks 27 of FIG. 1. Other locking mechanisms may be used if desired.

Handles such as front and rear handles 56 may be provided to allow the user to easily maneuver the cart.

The features of docking cart 14 may be provided using a stationary platform (e.g., in medical equipment such as an ultrasound workstation that is generally not moved). However, a movable docking cart 14 is often preferred, because it allows the ultrasound capabilities of the portable ultrasound unit and docking cart 14 to be shared among a number of different locations.

Figure 3:
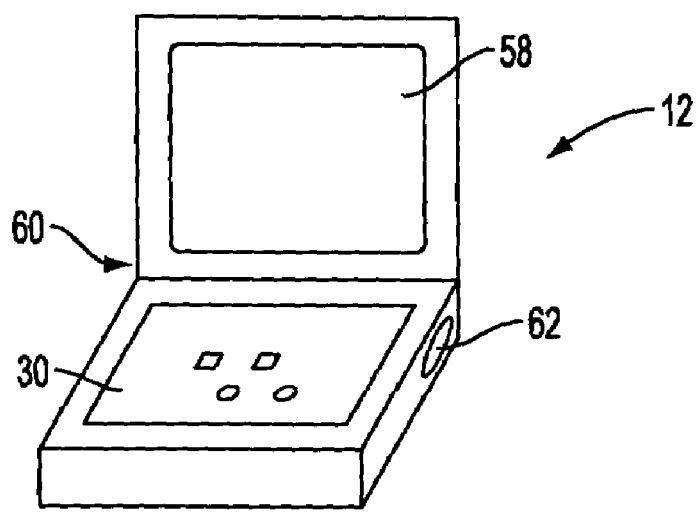
FIG. 3 is a perspective view of an illustrative portable ultrasound unit with an available ultrasound transducer port in accordance with the present invention.

An illustrative portable ultrasound unit 12 is shown in FIG. 3. As shown in FIG. 3, unit 12 may have a built-in flat panel display screen 58 (e.g., a color LCD display). This display, which may measure about 5–13 inches diagonally, may be used to display ultrasound images and other information when unit 12 is in operation. A hinge 60 may be used to allow the upper portion of portable unit 12 to fold down over the portable unit's user interface 30 when portable unit 12 is not being used. User interface 30 may include a track ball, joystick, touch pad or other pointing device, and buttons, knobs, keys, sliders, LEDs, speakers, microphones, and other suitable user interface equipment. Only a subset of such user interface devices are typically used on portable unit 12, due to space and weight considerations. For example, the sliders can be omitted to save space.

Figure 4:
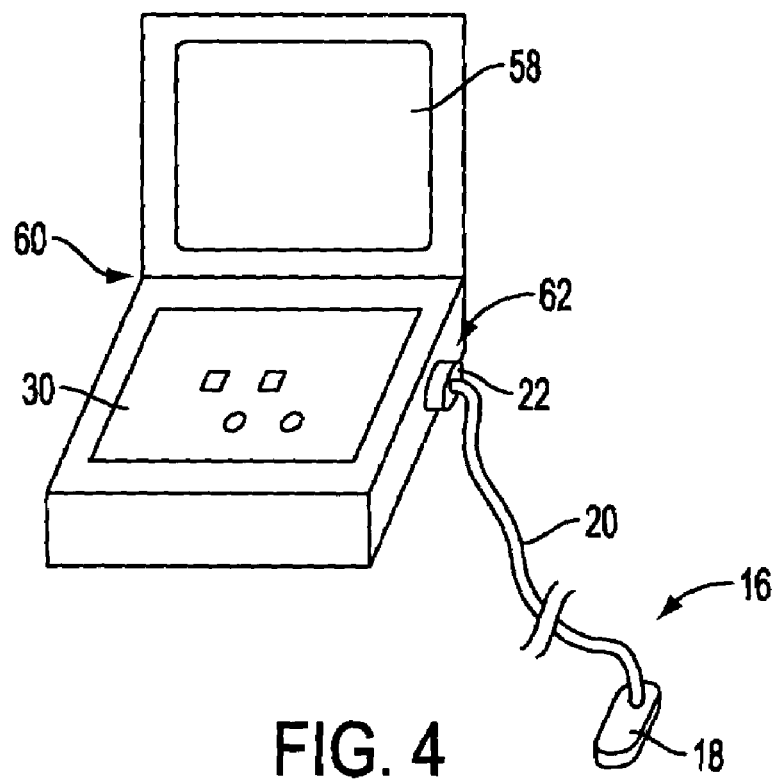
FIG. 4 is a perspective view of an illustrative portable ultrasound unit with an attached ultrasound transducer in accordance with the present invention.

Portable ultrasound unit 12 may have one or more transducer ports such as transducer port 62. As shown in FIG. 4, an ultrasound transducer 16 may be attached to the portable ultrasound unit 12 by using connector 22 to attach cable 20 and scanner head 18 to port 62. Different transducers 16 may be attached to unit 12 as needed depending on the ultrasound imaging task to be performed.

Figures 5, 6:
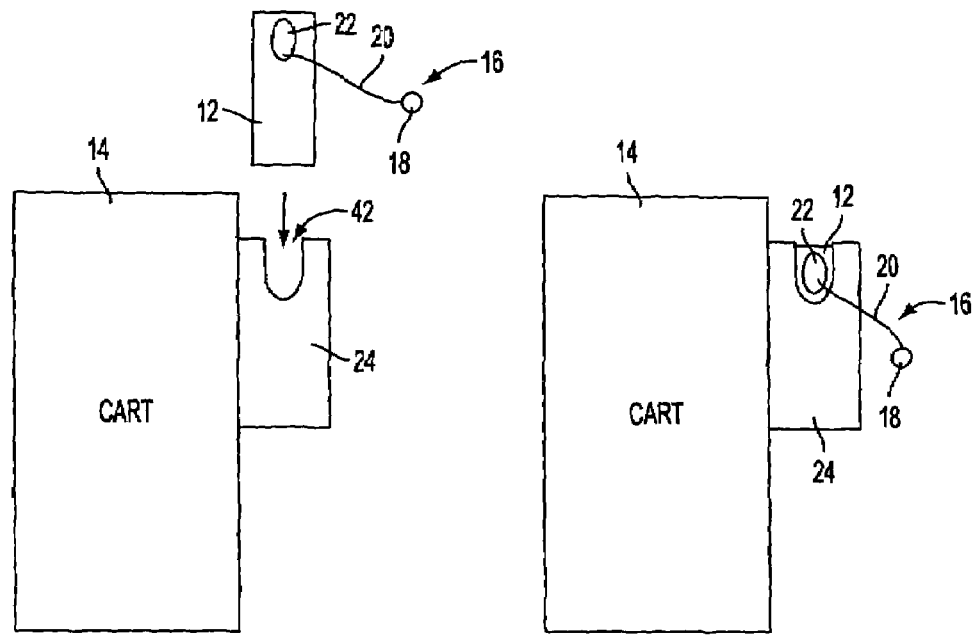
FIG. 5 is a diagram showing how a portable ultrasound unit may be inserted into a mating receptacle on a docking cart in accordance with the present invention.
FIG. 6 is a diagram showing how a docking cart receptacle for the portable ultrasound unit may be configured so as not to block the transducer port of the portable ultrasound unit in accordance with the present invention.

As shown in FIGS. 5 and 6, the docking structure 24 with which portable ultrasound unit 12 is attached to docking cart 14 may have a portion 42 that allows connector 22 and cable 20 of transducer 16 to remain attached to unit 12 even as unit 12 is mated with cart 14. This type of arrangement may be advantageous because it allows a user to continue using the same transducer that is attached to the unit 12 without interruption, even as the user transitions from using the user interface, display and other capabilities of the portable unit 12 to using the corresponding capabilities of the docking cart 14.

Figure 7:
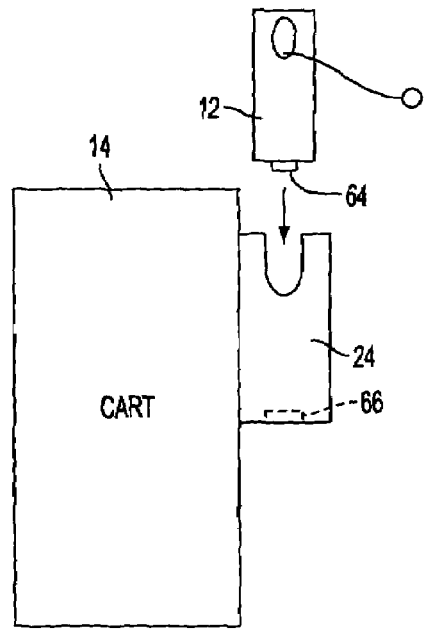
FIG. 7 is a diagram showing how a docking cart and portable ultrasound unit may have mating electrical connectors in accordance with the present invention.

If desired, the portable ultrasound unit 12 and docking cart 14 may have matching electrical connectors 64 and 66, as shown in FIG. 7. Connectors 64 and 66 may allow power and signals to be exchanged between unit 12 and docking cart 14. For example, ultrasound image data may be provided to docking cart 14 from unit 12 and power may be provided from docking cart 14 to unit 12 using connectors 64 and 66. Connectors 64 and 66 may be provided using one connector or multiple connectors. When transferring ultrasound imaging data that is still in "channel" form, the connectors may include numerous parallel electrical connectors (differential and single-ended) for transmitted data to the cart 14 corresponding to each of the scanner array elements (channels) in the transducer head 18. The communications functions provided by connectors 64 and 66 and their associated communications circuitry may also be provided using optical communications or RF communications arrangements.

Figure 8:
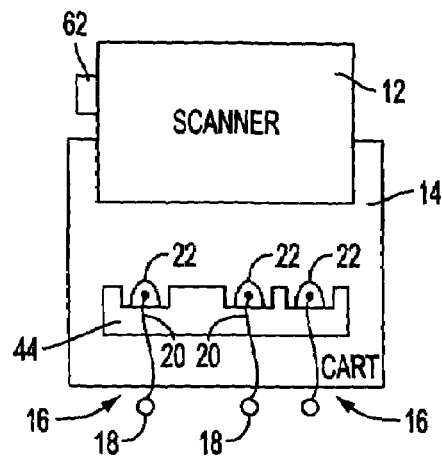
FIG. 8 is a diagram of an illustrative docking cart and portable ultrasound unit showing how the docking cart may have a holder for ultrasound transducer heads in accordance with the present invention.

An illustrative side view (partially schematic) of the docking cart 14 and attached portable ultrasound unit 12 (sometimes also called an ultrasound scanner or simply a scanner) is shown in FIG. 8. As shown in FIG. 8, unit 12 may be mounted to cart 14 so as to leave transducer port 62 accessible, even after unit 12 is connected to cart 14. Cart 14 of FIG. 8 has a transducer holding structure 44 that accommodates multiple transducers 16. With the illustrative arrangement of FIG. 8, the head 18 of each transducer 16 may be inserted into a respective holder receptacle in holding structure 44. The heads 18 and cables 20 that are associated with the transducers may hang below the transducer heads 18 or may be stowed in a storage area on cart 14, the user may select a desired transducer 16 (e.g., by selecting a transducer having the appropriate head 18 to suit a particular imaging task) and may then attach that transducer 16 to unit 12 by connecting its connector 22 to the exposed port 62.

Figure 9:
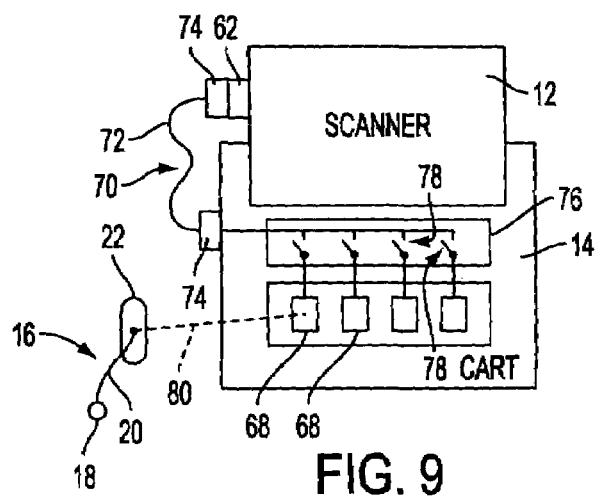
FIG. 9 is a diagram of an illustrative docking cart and portable ultrasound unit showing how transducer ports on the docking cart and a transducer port on the portable unit may be interconnected by a cable in accordance with the present invention.

If desired, cart 14 may have one or more transducer ports 68 (expansion ports) to which transducers 16 may be connected, as shown in FIG. 9. A given transducer 16 may be connected to one of the transducer ports 68 by attaching its connector 22 to that port, as shown by dotted line 80 in FIG. 9. An interface cable 70 or other suitable electrical connection may be used to connect the transducer port 62 of portable ultrasound unit 12 to the transducer ports 68. Interface cable 70 may have a cable portion 72 and connectors 74 that can be used to electrically connect the integral transducer port 62 on the portable unit 12 to the transducer ports 68 and other electronics of cart 14.

When cart 14 has more than one transducer port 68, a multiplexing circuit 76 may be used to connect a desired one of the cart's transducer ports 68 to the portable unit's transducer port 62 (or one of the portable unit's transducer ports 62 when unit 12 has more than one port). As shown in FIG. 9, multiplexing circuit 76 may have a number of switches 78 (e.g., electronic switching circuits), each of which is associated with a respective one of the transducer ports 68. The appropriate switch 78 may be activated by any suitable technique. For example, the user may manually activate a button or other control that directs the processor in the cart 14 to close the appropriate switch 78. Alternatively, the cart 14 may automatically sense which transducer head is being used (e.g., because an associated switch or sensor has been triggered in the holder 44 or on the transducer head 18). After the multiplexer 76 is used to interconnect the appropriate transducer connected to one of the transducer ports 68 to the transducer port 62 of the portable ultrasound unit 12, the portable ultrasound unit 12 may communicate with that transducer via port 68, interface cable 70, and port 62. This type of arrangement allows the analog-front-end and related electronics of the portable ultrasound unit 12 to be used without needing to use (or even provide) these capabilities in docking cart 14, although such capabilities may be provided in cart 14 as a supplemental or redundant feature if desired.

Figure 10:
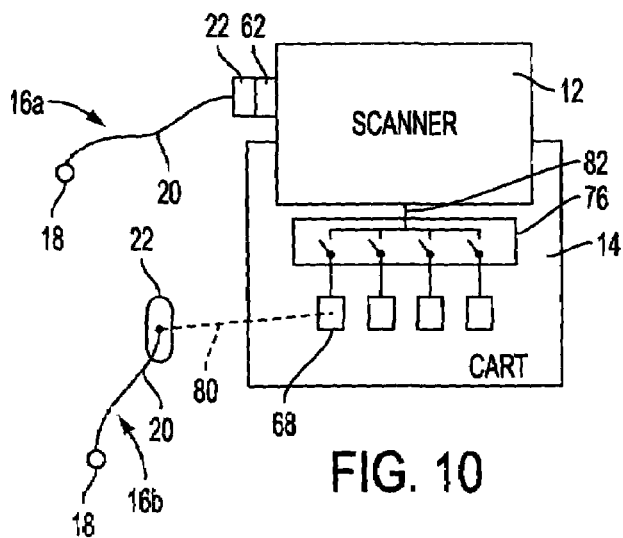
FIG. 10 is a diagram of an illustrative docking cart and portable ultrasound unit showing how transducer ports on the docking cart may be interconnected with the processing electronics of the portable unit by an internal electrical connection in accordance with the present invention.

As shown in FIG. 10, the portable ultrasound unit 12 and docking cart 14 may be electrically connected using an electrical connection 82 that does not require the use of the transducer port 62 of unit 12. This type of arrangement may leave the transducer port 62 free to be used by another transducer 16 or at least allows that transducer 16 to remain attached to the portable ultrasound unit 12 during the time in which the unit 12 is docked in the docking cart 14. As shown in FIG. 10, for example, transducer 16a may be connected to port 62 while another transducer 16b may be connected to one of the cart's transducer ports 68.

With the interface cable arrangement of FIG. 9, the transducer port 62 of the portable ultrasound unit 12 remains in use, but receives signals from a new transducer port (e.g., one of the expansion transducer ports 68 on cart 14). With arrangements of the type shown in FIG. 10, the electrical connections between the unit 12 and cart 14 (shown by line 82) allow a connection between transducer 16b and the internal electronics of portable unit 12 to be made without using port 62 (and transducer 16a). In general, it is not desirable to encumber unit 12 with excess capabilities for handling transducer inputs, so unit 12 will typically only have sufficient circuitry to handle a single active transducer 16 at a time. Accordingly, the user of the equipment in FIG. 10 may be provided with an opportunity to specify which transducer 16 is to be used (either the transducer connected to the unit's port 62 or a particular one of the multiplexed transducers connected to the cart's ports 68). The user selection of the transducer connection may be made using user interface 134 (e.g., by a knob, switch, or button or via interactions with on-screen options displayed on a display such as display 28 of FIGS. 1 and 2).

Figure 11:
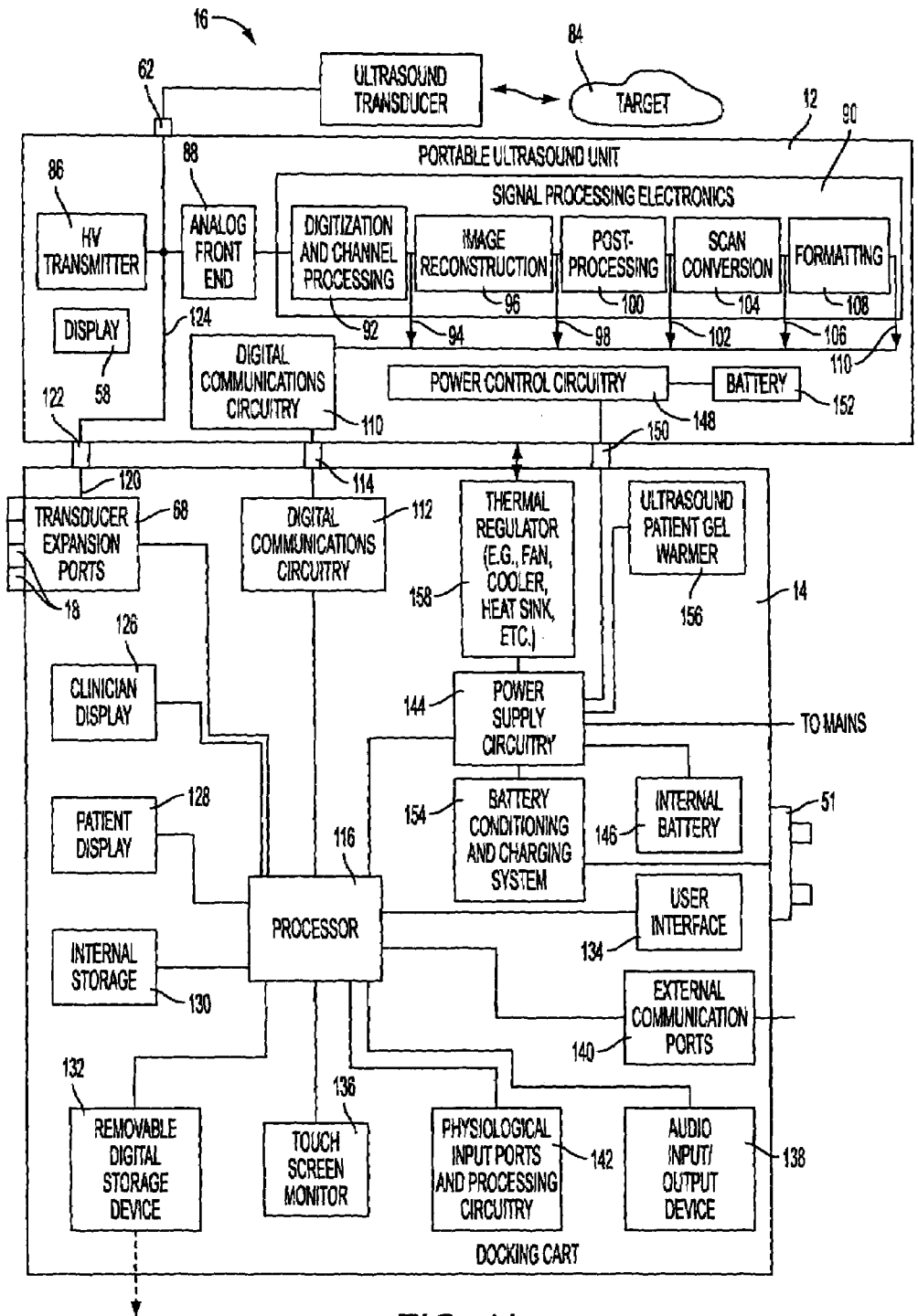
FIG. 11 is a schematic block diagram of an illustrative docking cart and portable ultrasound unit in accordance with the present invention.

A schematic diagram of an illustrative portable ultrasound unit 12 and docking cart 14 are shown in FIG. 11. Ultrasound transducer 16 may be used to gather ultrasound images of a medical patient or other suitable image target 84. The portable ultrasound unit 12 has electronic circuitry for generating ultrasonic acoustic waves that are launched into target 84 and has electronic circuitry for gathering and analyzing reflected acoustic waves to form corresponding ultrasound images. High-voltage transmitter 86 generates drive signals for the piezoelectric scanner elements in ultrasound transducer 16. The resulting acoustic waves are reflected from the structure of target 84. The scanner elements of transducer 16 convert the reflected acoustic waves into electrical signals, which are processed by input circuitry in unit 12.

The input circuitry in portable ultrasound unit 12 may include an analog front end 88 and other signal processing electronics 90. The circuitry of analog front end 88 helps to condition the analog signals from transducer 16 prior to digitization of these signals by signal processing electronics 90. Transducer 16, which may either be directly connected to unit 12 or which may be connected to unit 12 through the docking cart's expansion ports 68, may have numerous (e.g., 100 or more) individual scanner elements, each which generates a signal on a separate "channel." Accordingly, analog front end 88 may have circuitry that processes the analog input signals for each channel in parallel. Analog front end circuitry may include amplifier circuitry for amplifying signals detected by the transducer and may include analog filter circuitry for filtering out unwanted signals (e.g., based on their frequency). The conditioned analog signals from analog front end 88 may be converted to digital signals by digitization and channel processing circuitry 92.

Digitization and channel processing circuitry 92 may have analog-to-digital converters, buffer circuitry, and processing circuitry that digitize each channel of data in parallel, resulting in a total digital data throughput of about 10–1000 Gbps (or other suitable rate). Digitization and channel processing circuitry 92 may enhance the signal-to-noise ratio of the ultrasound image data by performing channel-domain processing tasks such as deconvolving coded signals to filter out unwanted signals. Following processing by digitization and channel processing block 92, the ultrasound image signals may be provided at output 94 as "channel data," so-called because the data at this stage is still available on individual channels, each corresponding to a respective transducer array piezoelectric element.

The channel data must be processed further before a displayable image is created. Image reconstruction block 96 of signal processing electronics 90 may be used to perform image reconstruction tasks (also called "beam formation tasks"). The resulting data signals at output 98 may be referred to as "RF data" (data at a processing point after beam-formation, but prior to sampling and detection). The RF data at output 98 still has both amplitude and phase information.

Further processing of the image data may be carried out using the post-processing portion 100 of electronics 90. The resulting image data provided at output 102 (called "detected data") contains amplitude information, but no longer contains independent phase information.

The "detected data" image data may be processed further by the scan conversion portion 104 of electronics 90 to produce "scan-converted data" at output 106. The detected data processing performed by portion 104 may involve the use of acoustic-domain processing techniques that are based on a knowledge of the physical geometry of transducer 16. Scan-converted data may be displayed as an ultrasound image on a display such as display 58, 126, or 128.

The scan-converted data produced at the output 106 of scan-conversion electronics 104 may be processed by formatting electronics 108 to produce corresponding "formatted image data" at output 110. The formatted image data may be in a format suitable for display on a display such as display 58 or displays 126 or 128. During formatting with electronics 108, content such as text or graphic overlays (e.g., annotations such as physician-entered annotations, time/date stamps, etc.) may be merged with the image to be displayed.

The digital image data from signal processing electronics 90 of portable ultrasound unit 12 may be provided to docking cart 14 in a number of different forms. Portable ultrasound unit 12 may have digital communications circuitry 110 for supporting communications with cart 14 and cart 14 may have digital communications circuitry 12 for supporting communications with portable unit 12. A connector 114 (partly implemented using a connector on unit 12 and partly implemented using a connector on cart 14) may be used to interconnect circuitry 110 and circuitry 112.

Digital communications circuitry 110 and 112 may be used to support any suitable digital communications format. For example, data may be exchanged using serial protocols, parallel protocols, protocols for universal serial bus (USB) communications, IEEE 1394 (FireWire) communications, etc.

The image data supplied to cart 14 by portable ultrasound unit 12 may be provided in a relatively unprocessed form (e.g., as channel data at output 94), in a relatively processed form (e.g., as formatted data at output 110). Data may also be transferred from unit 12 to cart 14 after an intermediate level of processing has been performed (e.g., as data at one or more of outputs 98, 102, and 106). Providing image data to cart 14 in a relatively unprocessed form may be advantageous when it is desired to retain a relatively large amount of flexibility for subsequent cart-based processing and when it is desired to avoid potentially irreversible losses of signal quality. Providing image data to cart 14 in a relatively processed form may be advantageous when it is desired to reduce the processing burden on cart 14 and when this benefit outweighs the potential loss of flexibility in downstream signal processing that results from preprocessing the data.

The image data that is provided from unit 12 to cart 14 using communications circuitry 110 and 112 may be provided in one format or only a few different formats (to simplify the processing circuitry in signal processing electronics 90). This image data may also be provided in many formats (e.g., all of the formats shown in FIG. 11).

If desired, the image data from unit 12 may be provided to cart 14 in the form of "channel data" at output 94. Channel data includes signal samples gathered from each of the active piezoelectric elements in transducer 16. The channel data is image data that has been digitized by the analog-to-digital converter circuitry of digitization and channel processing circuitry 92 of electronics 90, but which has not yet undergone the beam formation process implemented by image reconstruction electronics 96. An advantage of providing image data from portable unit 12 to cart 14 as channel data is that this allows the processing capabilities of the cart 14 to be used in handling the beam formation (image reconstruction) process.

Because the cart 14 may have a relatively powerful processor 116, the cart may, if desired, use such processing capabilities to perform more accurate or complete beam formation processing operations than would be possible using only the processing capabilities of unit 12. Moreover, the beam formation operations of the cart may, if desired, be controlled by the user. For example, the cart may provide users with the ability to interact with on-screen options to make changes to the beam formation operation (e.g., through user-adjustable parameters). The user may, for example, make changes in the way the cart's processor handles velocity data, amplitude data, or other channel-based signal information.

If desired, the image data from unit 12 may be provided to cart 14 in the form of "RF data" at output 98. RF image data is the data that has been through the image reconstruction process, but has not been sampled and detected. (The sampling and detection processes are performed by post-processing electronics 100.) RF image data still includes intact phase information. An advantage to providing image data to cart 14 in the "RF data" format is that this allows the cart's processor to perform phase-related image-enhancement operations that are not possible once the phase information has been lost (as is the case with detected data). Substantially less bandwidth is required to transfer image data between circuitry 110 and 112 in the form of RF data than in the form of channel data.

If desired, image data can be provided from unit 12 to cart 14 in the form of "detected data" at output 102. An advantage of providing data as detected data rather than as RF data is that less processing is required to make the detected data displayable for the user. The detected data output stage of processing electronics 90 is the last stage at which an image for the display screen (e.g., the cart's display) can be generated in any desired native resolution without risk of compromising image quality (e.g., through resolution or image content losses). Detected data may, however, still be processed using acoustic-domain image processing techniques. If image data is provided from unit 12 to cart 14 at the "detected data" stage, rather than after processing the data further, cart 14 can still be used to implement image processing tasks that are based on considerations of scanner (transducer head) geometry.

An additional reduction in the processing burdens on cart 14 can be attained by providing image data from unit 12 to cart 14 in the form of "scan-converted data" at output 106. Scan-converted data is data that has been converted from a format based on scanner geometry (detected data) to a user-display-oriented format. Image processing can still be performed on scan-converted data (if desired) using the amplitude information contained in the scan-converted data. For example, x-y filtering operations may be performed on the scan-converted data. The scan-converted data at output 106 does not contain physician annotations or other overlay information. That information may be added by formatting electronics 108. An advantage of providing image data to cart 14 in the form of scan-converted data is that the cart need only annotate the data (if desired) and convert the data to the proper screen format before displaying the data on one of the cart's displays. Because scan-converted data does not include annotations, this arrangement preserves the ability of the cart to display unannotated data.

Image data may also be provided from unit 12 to cart 14 in the form of "formatted image data" at output 110. Formatted image data includes annotations (e.g., automatically-generated annotations and annotations based on user input). Providing the image data to the cart as formatted image data reduces the image processing requirements of the cart to an extremely low level. Both scan-converted data and formatted image data have already been converted to a resolution that is specific to the screen format of the display 58 of portable ultrasound unit 12, so this data is preferably converted (e.g., by processor 116) to a format that is suitable for presentation on the displays of cart 14. Formatted image data may be formatted (by either unit 12 or subsequently by cart 14) to accommodate standards such as JPEG, TIFF, BMP, MPEG, or other suitable formats.

The processing capabilities of the cart 14 may be provided by processor 116 and other components of the type shown in FIG. 11. Processor 116 may be based on one or more integrated circuits and other components. Processor 116 may, for example, be based on devices such as microcontrollers, microprocessors, personal computer boards, digital signal processors, programmable logic devices, application specific integrated circuits, memory devices, etc. In general, the capabilities of processor 116 may be used to enhance the processing capabilities of portable ultrasound unit 12, which are limited by size and weight considerations. Processor 116 may perform image processing tasks and may also serve as an embedded controller that controls the overall operation of cart 14. Functions controlled by processor 116 include coordinating input and output operations involving the user, ultrasound transducers, internal components, and peripheral devices.

As described in connection with FIGS. 8, 9, and 10, cart 14 may have one or more transducer expansion ports 68. In FIG. 11, the connectors 118 that are used to attach transducers 16 to ports 68 are shown as being connected to ports 68 from the exterior of cart 14. To use a given transducer 16 that is connected to one of the transducer expansion ports 68, processor 116 may activate multiplexer circuitry (e.g., multiplexer circuitry associated with expansion ports 68 such as the multiplexer circuitry 76 of FIGS. 9 and 10) that switches a desired transducer 16 to communications line 120.

Communications line 120 may be connected to high-voltage transmitter 86 by connector 122 and line 124. High-voltage drive signals that are generated using the portable unit's HV transmitter 86 may be provided to a transducer 16 that is connected to one of the cart's expansion ports 68 via line 124, connector 122, and line 120. Input signals from the same transducer may be routed through the expansion port 68 to the analog front end 88 of the unit 12 via communications line 120, connector 122, and communications line 124. The expansion port arrangement therefore allows the same high-voltage transmitter and analog front end (and some or all of the rest of signal processing electronics 90 such as digitization and channel processing circuitry 92) to be used to handle signals from both the transducer 16 that is connected to connector 62 of unit 12 and a transducer 16 that is connected to the expansion port.

Connector 122 (which may be partly implemented in unit 12 an partly implemented in cart 14) may be an electrical connector capable of passing numerous parallel channels of high-frequency signals having a large dynamic range (e.g., 160 dB or more). Connector 122 may, for example, be formed using the same types of electrical contacts and circuits used by connector 62 (FIGS. 3 and 11) when connecting the main transducer 16 to portable unit 12.

The expansion port capabilities of cart 14 allow the larger size of the cart 14 to be used to overcome some of the size constraints faced by the portable ultrasound unit. With the expansion ports 68 of the cart 14, a user may attach multiple transducers 16 to the unit 12. The multiplexer circuitry that determines which of the transducers (main transducer 16 or one of the transducers connected via a given connector 118 attached to one of ports 68) is connected to the input and output electronics of the portable unit (e.g., HV transmitter 86 and analog-front-end 88) may be manually configured (e.g., through user interactions with the processor 116 through on-screen options) or may be automatically detected and configured (using mechanical or electronic detection of the presence or absence of a transducer at the ports 68).

Although the shown as having four transducer expansion slots 118 in FIG. 11, the cart's transducer expansion port 68 may accommodate any suitable number of transducers if desired.

The docking cart 14 may have one or more displays that supplement or replace the display capabilities of the portable ultrasound unit 12. For example, docking cart 14 may have one or more clinician (user) displays 126. Such displays may be larger than would be desired on a portable device due to the size, weight and power constraints imposed by portability. More information may be displayed on the cart's displays than on the display of the portable unit 12. For example, additional information may be included on cart display 126 (e.g., additional physician annotations, additional cart-generated annotations or overlay information, etc.). Additional image resolution an image content may be provided. The cart may, for example, display an image on a display 126 using the native resolution of that display (e.g., by using the cart's processor 116 to format the detected data from the portable unit into data in the desired native resolution).

The cart 14 may also include one or more patient displays such as patient display 128. A patient display is intended to be viewable by a patient during use of the cart 14 and portable unit 12 in performing ultrasound procedures. Patients cannot always see the monitors of traditional ultrasound units and are often not encouraged to do so because the monitors are awkwardly placed and because the images displayed on the monitors contain potentially disturbing physician annotations. The patient display 128 may be placed on an articulating arm or other support that makes it easy for the patient to view the image on the monitor without hindering the ability of the clinician to perform the ultrasound procedure. Moreover, some or all of the supplemental information (e.g., text and graphic overlays such as clinician annotations) that are displayed for the user (e.g., the physician or other clinician) on clinician display 126 may be suppressed (not displayed) by the processor 116 before displaying the image for the patient. The images displayed on the patient display 128 will therefore be less likely to cause undue concern on the part of the patient viewing the images.

The docking cart 14 may have internal storage 130. The internal storage may be formed using a hard drive, memory circuits (e.g., flash, RAM, ROM, EPROM, EEPROM), or any other suitable memory or storage device. Storage 130 may be used to store patient record data and image data (including stills and moving images) from portable unit 12.

The docking cart 14 may also have removable storage. Cart 14 may, for example, have one or more removable storage devices 132 such as magneto-optic drives, diskette drives, compact flash slots or other memory card readers, writable CD or DVD drives, tape drives, etc. Removable storage media may be used when it is desired to archive a patient record or other information (e.g., an ultrasound video clip and associated physician annotations, etc.).

Docking cart 14 may have one or more user interface devices (shown generally as user interface 134 in FIG. 11). Displays such as clinician display 126 and patient display 128 may be used to display images and other information. If desired, one or more of the displays may be touch-sensitive, as shown by touch-screen monitor 136. When cart 14 has a touch-screen monitor such as monitor 136, "soft menus" (e.g., user interface menus that processor 116 dynamically constructs out of on-screen options on the touch screen) can be used to provide a user of the cart 14 with user interface support. All or part of a given monitor may be provided with touch-screen capabilities.

An advantage of using a touch screen as a user interface for docking cart 14 is that this arrangement can help reduce clutter in the user console area. Ultrasound system operation can require many user adjustments. However, during certain modes of operation only a subset of the user controls are active. When the touch screen is used, inactive user control options can be hidden from view. Because inactive controls need not be displayed, they can either be hidden from view entirely (i.e., not displayed) or can be displayed in a way that indicates clearly to the user that those functions are currently inactive (e.g., by displaying the options with a reduced level of visibility on the screen relative to the options that remain active, by changing their color, etc.).

User interface 134 may also contain sliders (e.g., one or more sets of gain-depth-compensation sliders), knobs, buttons, keys (e.g., numeric keys, special functions keys, a full-size keyboard, etc.), and pointing devices (e.g., a mouse, trackball, joystick, keyboard-mounted pointing stick, touchpad, etc.). The keyboard of user interface 134 may be used for data entry (e.g., patient data entry) and image annotation. An advantage of providing a full-size keyboard on cart 14 is that this allows easier data entry than the typically smaller user interface 30 of unit 12 (see, e.g., FIG. 3). The pointing device and other controls may be used to navigate among various on-screen options that are displayed on displays such as displays 126 and 128. Such on-screen options may, for example, allow the user to select which information is to be displayed on the cart's displays, to select which imaging modality is being used, to control settings, etc. Two sets of sliders may be used—one for adjusting the vertical gain/brightness of the display image and a second for adjusting the lateral gain/brightness of the display image. Special function keys may be used in user interface 134 to provide users with the ability to make single-key selections of options (e.g., to perform functions such as adjusting luminance curves, L/R invert, U/D invert, display format adjustment, sweep speed, acoustic output, Doppler gate size, etc.). These are merely illustrative user interface devices and ways in which such devices may be used to control the functions of cart 14 and portable unit 12. Any suitable user interface arrangement may be used to allow one or more users to interact with docking cart 14 and unit 12 if desired.

Audio input/output device 138, which is shown separately in FIG. 11, is a user interface device that may be used to present audio information to the user (e.g., the audio track associated with the spectral Doppler mode of operation of unit 12 that is picked up by a microphone associated with unit 12 or a microphone associated with cart 14). Because audio input/output device 138 is not limited by the same size and weight considerations that limits audio equipment on unit 12, audio input/output device 138 may include high-quality audio speakers (e.g., speakers with a frequency response of about 250 Hz to 5 kHz or about 20 Hz or 30 Hz to 20 kHz). Audio input/output device 138 may also include one or more microphones that receive user audio inputs (e.g., voice annotations for a patient record, voice commands that are processed by a voice recognition module implemented on processor 116, etc.).

Docking cart 14 may have one or more external communications ports 140. The communications circuitry of ports 140 may be used to provide an interface between processor 116 and the other components of cart 14 and peripheral devices such as printers, plotters, recording devices (e.g., video recording devices such as VCRs or recordable DVD equipment), network equipment, telecommunications equipment, external displays, external storage devices, etc. Ports 140 may provide support for RS-232 signals and analog video. Ports 140 may also provide support for digital audio and video (and other data). Ports 140 may support USB communications (e.g., USB 1.1 or 2.0), FireWire, parallel communications, serial communications, 10-BaseT, 100-BaseT, 1000-BaseT, VGA, Digital Video, NTSC, PAL, S-video, wireless communications such as IEEE 802.11a, IEEE 802.11b, etc. The ports 140 allow processor 116 to communicate with networks such as wired or wireless hospital LANs. Docking cart 14 can use ports 140 to monitor the status of the current network environment, which allows cart 14 to determine when cart 14 is moved to a new network or a new portion of its current network.

Docking cart 14 may also have physiological input ports and processing circuitry 142. The input capabilities and processing capabilities of physiological input ports and processing circuitry 142 may be used to gather (and process) information from external medial equipment.

As an example, physiological input ports and processing circuitry 142 may be used to handle cardiac information. The portable ultrasound unit 12 and docking cart 14 may be used to make ultrasound measurements during cardiac exams. During this type of study, it may be desirable to be able to synchronize ultrasound data collection operations with the phases of the cardiac cycle. Cardiac information for synchronization may be provided from an external EKG machine, from an implanted pacemaker or other cardiac device (e.g., based on internal cardiac information gathered using real-time telemetry), or may be provided using any other suitable equipment.

The cardiac information may be processed by the attached equipment. For example, EKG equipment connected to port 142 may process the raw cardiac signal from a patient to identify various portions of the cardiac signal and to generate corresponding heart signal markers. If desired, the cardiac signal may be provided directly to the cart 14 (after appropriate signal conditioning) and the cart's processing circuitry 142 may be used to identify different portions of the cardiac signal and to generate corresponding heart signal markers.

After the cardiac signal has been analyzed (by the external EKG equipment or by processing circuitry within cart 14), and corresponding markers have been generated, the marker information (or other suitable timing information) may be used by the docking cart 14 and unit 12 to synchronize the ultrasound operations of the cart 14 and unit 12 with the functioning of the heart. For example, cardiac ultrasound images or images of a blood vessel may be captured during a particular portion of the cardiac cycle or scans may be initiated in synchronization with particular cardiac events.

If desired, processor 116 can display the cardiac markers and cardiac signals (e.g., the EKG signals) on the cart's displays such as displays 126 and 128. Processor 116 can also store this information in storage 130 or on the storage media associated with removable storage device 132 (e.g., in the form of a patient record). To ensure that the ultrasound scanning operations of unit 12 are properly synchronized with the cardiac signal, processor 116 can pass the cardiac markers and cardiac signals to portable unit 12 for processing by the processing circuitry of unit 12 or processor 116 may send timing or other synchronization or control signals to unit 12 that unit 12 can use to synchronize its operation.

The physiological input ports and processing circuitry 142 of cart 14 can handle cardiac information, information from blood oxygen sensors, information from pulse sensors, information from respiration sensors, or any other suitable physiological equipment. In general, some or all of the processing of the raw sensor signals can be performed in the external equipment and corresponding digital information signals can be provided to processor 116 via port 142. If desired, processing circuitry 142 may be used to handle signal conditioning and physiological data analysis tasks. Physiological data (or digital signals generated in response to processing the physiological data) may be shared with portable ultrasound unit 12 (e.g., using a communications link between unit 12 and cart 14 that is supported by the functions of digital communications circuitry 110 and 112). This information may also be stored in the form of patient records (e.g., using storage 130 or 132) or may be transmitted to a network (e.g., a hospital network connected to cart 14 via one of external communications ports 140).

Docking cart 14 may draw power from an AC wall outlet (mains) or from an internal battery 146. Power supply circuitry 144 may be used to distribute power from the external supply or from the internal battery 146 to the components of cart 14. Power supply circuitry 144 may also supply power (from an external AC supply or from internal battery 146) to power control circuitry 148 of portable ultrasound unit 12 via connector 150. Power control circuitry 148 of portable ultrasound unit 12 may be used to distribute power from cart 14 or from internal battery 152 to the components of unit 12. Unit 12 may also use power from an AC source when not using power from cart 14 or battery 152. Power supply circuitry 144 may sense which type of AC source is connected to cart 14 (e.g., 110 V, 60 Hz or 220 V, 50 Hz) and may adjust automatically to accommodate the characteristics of the AC source.

When cart 14 is not connected to a source of AC power, the cart's internal battery 146 may be used to operate the cart's components and may (if desired) be used to supplement or replace the power supplied by the unit's battery 152. The cart's internal battery allows the cart to be readily transported from one room to another in a hospital or other establishment, without requiring that the user locate the cart near to an available wall outlet. The user can connect or disconnect the cart and AC power source at any time without interrupting the cart's operation.

The power supply circuitry 144 and power control circuitry 148 may be used to recharge the batteries 146 and 152 when AC power is available. Cart 14 may also have a battery conditioning and charging system 154 (and associated battery ports 156). The system 154 may be used to condition and charge the portable ultrasound unit's batteries (i.e., batteries such as internal battery 152 that have been removed from the unit 12). The battery charger of cart 14 may also be used to condition and charge other batteries (e.g., batteries for other portable medical equipment). One suitable location for the battery charging ports or receptacles is shown by the position of batteries 50 in their associated receptacles 51 on cart 14 of FIG. 2. The battery conditioning and charging system 154 and associated receptacles 51 provide a convenient mechanism for providing users of portable ultrasound unit 12 with a supply of fresh batteries in a convenient location. The conditioning operations of system 154 (which involve the use of multiple charge-discharge cycles to recondition weak or aged batteries) may be performed when the battery is determined to be weak, when the user initiates the conditioning process, or at any other suitable time. Batteries such as battery 152, battery 146 and batteries 50 (FIG. 2) may be based on any suitable battery chemistry, wet or dry. Fuel cell technology (e.g., hydrogen-based or methane-based fuel cells) may be used for the batteries if desired.

Ultrasound acoustic impedance matching gel is used to improve the efficiency of the acoustic impedance match between the face of transducer 16 and the target 84 (e.g., the tissue of the patient). The gel is typically applied directly to the skin of the patient. Docking cart 14 may have an ultrasound patient gel warmer 156 to warm the gel to a comfortable temperature before the gel is applied to the patient. The warmer 156 may warm the gel slightly above the ambient temperature of the room (e.g., to about 37° C.+/−5° C.). The gel warmer may be integrated into a cup-holder shaped structure (e.g., for holding plastic bottles of gel) or may have any other suitable shape.

The gel warmer 156 may have a resistive or inductive heating element powered by power supply circuitry 144 or may use passive heating (e.g., the gel may be warmed by virtue of being located adjacent to a source of passive heating such as a warm portion of the cart's electronics, a heat sink, a fan outlet, etc.).

Portable ultrasound unit 12 is generally more exposed to the ambient atmosphere when used as a stand-alone unit than when unit 12 is connected to cart 14 and placed in a receptacle such as holder 24 (FIG. 1). Exposure to surrounding air tends to cool unit 12. Unit 12 may therefore experience a temperature rise when placed in a confined environment without supplemental cooling. Accordingly, docking cart 14 may have a supplemental thermal regulator 158 that helps to control the temperature of portable ultrasound unit 12 when unit 12 is connected to cart 14. (Docking cart 14 may also use thermal regulation devices to control the temperature of components in cart 14). Supplemental thermal regulator 158 may use passive or active heat regulation techniques to prevent unit 12 from overheating when connected to cart 14. Suitable active thermal regulation devices that may be used in thermal regulator 158 include fans (for providing cooling by forcing air across the unit 12), Peltier-effect coolers, water-cooling structures, etc. Suitable passive thermal regulation approaches may be implemented by providing cart 14 with supplemental heat sinks, air channels for allowing unit 12 to be air cooled despite being connected to cart 14, heat pipes, etc.

Figure 12:
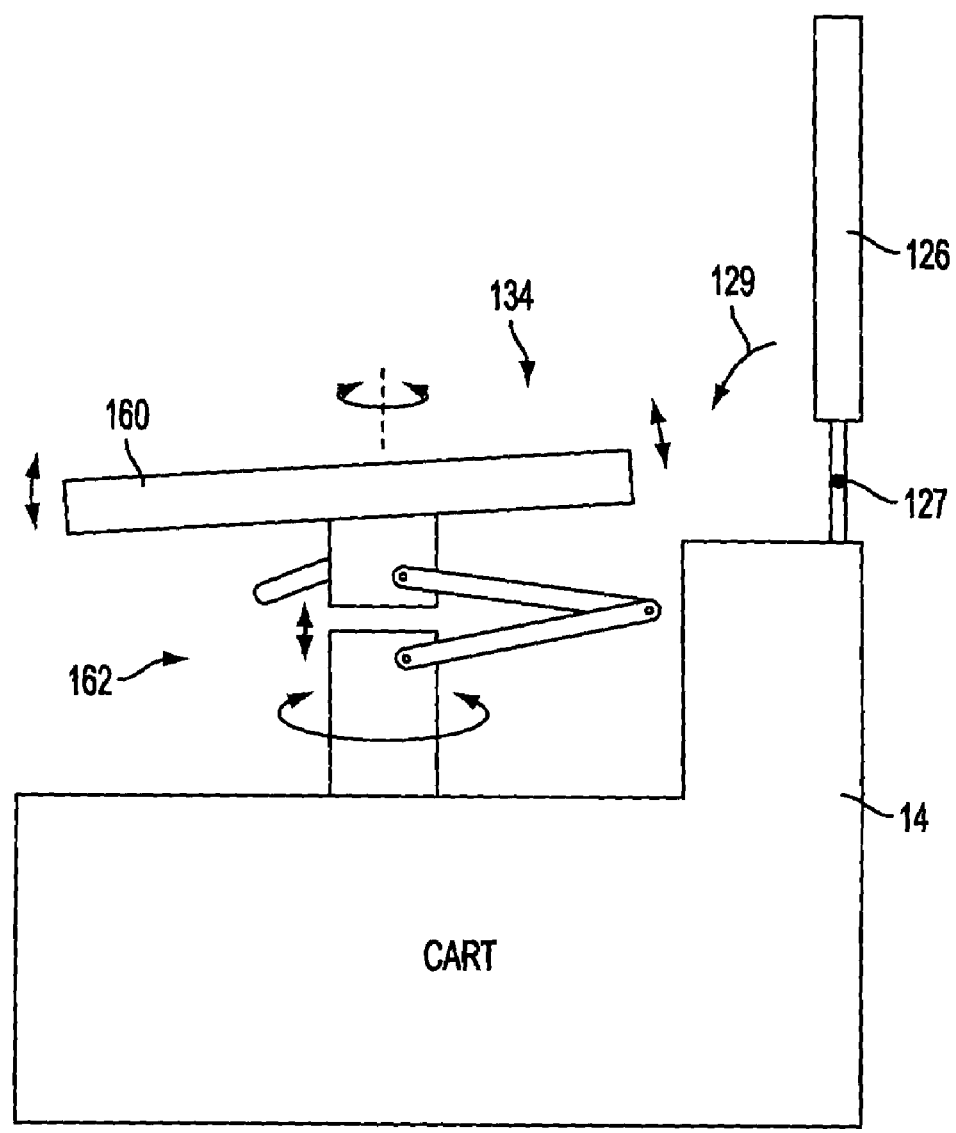
FIG. 12 is a side view of an illustrative mount for a control panel on a docking cart in accordance with the present invention.

As shown in FIG. 12, the docking cart user interface 134 may have an adjustable control panel or workspace consol 160. The control panel or consol is an illustrative user interface that may include control knobs, buttons, keys, and other user interface controls. As shown in FIG. 12, interface 160 may be mounted using a mounting structure such as mounting structure 162 that allows the position of the interface to be tilted, rotated, raised, lowered, or otherwise moved or adjusted in a number of different possible directions and orientations. Providing the docking cart 14 with an adjustable user interface arrangement such as the adjustable user interface arrangement of FIG. 12 provides users with an ergonomic interface for interacting with the cart 14. The user-adjustable user interface mounting structure arrangement of FIG. 12 is merely illustrative. Any suitable mounting structure may be used to allow the position of some or all of the user interface controls of cart 14 to be adjusted by the user if desired. For example, the mounting structure 162 can be configured to allow the user interface to be adjusted in only one dimension (e.g., a tilt only), in two dimensions (e.g., horizontal and vertical tilting), or in more dimensions (e.g., in five dimensions).

If desired, physician display 126 may have a hinge 127 or other mounting structure that allows display 126 to fold down out of the way, as shown by arrow 129. Folding down display 126 onto the consol of cart 14 reduces the height of display 126, so that cart 14 can be transported (e.g., in a minivan or sport-utility vehicle) with a lower risk of damaging display 126.

Figure 13:
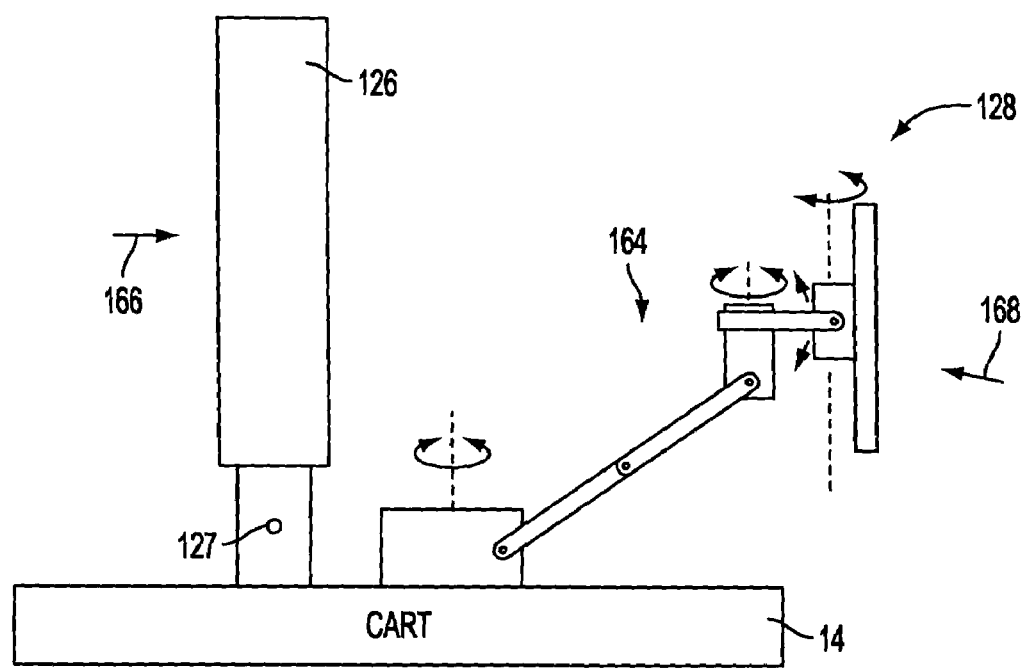
FIG. 13 is a side view of an illustrative mount for mounting a display to a docking cart in accordance with the present invention.

As shown in FIG. 13, patient display 128 may also have an adjustable mounting structure 164. As with mounting structure 162 of FIG. 12, the mounting structure 164 of FIG. 13 can be configured to allow the display 128 to be adjusted in only one dimension (e.g., a tilt only), in two dimensions (e.g., horizontal and vertical tilting), or in more dimensions (e.g., in five dimensions). In general, any suitable mounting structure may be used to allow the position of patient display 128 to be adjusted by the user if desired. As shown in FIG. 13, the patient display 128 can (in at least some orientations) be viewed from very different directions than the monitor 126. For example, clinician display 126 can be viewed in direction 166 from the front of cart 14, whereas patient display 128 can be viewed from the rear of cart 14 in direction 168. This type of arrangement allows the patient to view ultrasound images without disturbing the view of the physician. The physician display 126 may be mounted on a swivel mount or a user-adjustable mounting structure such as mounting structure 162 or 164.

The docking cart 14 may have a number of security features. For example, cart 14 may be provided with a locking mechanism to lock the portable ultrasound unit 12 into place in the cart 14. The docking cart 14 may also have a security cable or other structure that allows the cart itself to be locked to another structure. The wheels 26 (FIG. 1) may have manually or automatically actuated locks 27 that may be used to lock the swiveling and/or rotation of wheels 26.

Cart 14 may automatically lock wheels 26 or may issue an alarm when it is determined that cart 14 has been removed from its authorized location or is being used by an unauthorized user. For example, cart 14 may issue inquiries through communications port 140 to determine whether or not cart 14 is in communication with an authorized network. The inquiries may be coded messages sent through an Ethernet connection, may be inquiries that determine whether or not cart 14 is in wireless connection with the cart's home network, etc. If cart 14 has been moved from its normal location (e.g., if cart 14 has been stolen), cart 14 (e.g., processor 116 using ports 140) can detect that the network environment has changed, and can take appropriate actions. If desired, the cart 14 can monitor the status of the cart's communications environment to determine whether or not the working environment of cart 14 changes for more than a threshold period of time. With this approach, short problems with the cart's network connection will not generate false alarms. The period of time for which an unknown communications environment is allowed to exist before the cart takes appropriate actions can be configured by the user.

Actions that may be taken by processor 116 when processor 116 detects unauthorized movement or use of cart 14 include shutting down some or all of the operations of cart 14 to prevent continued unauthorized use of cart 14. A warning message may be displayed on display 126. If an appropriate password or other authentication information is provided, the shut-down process may be overridden. The processor 116 can (as an alternative to disabling the functions of docking cart 14 or in addition to such disabling operations) send a message such as an email message via port 140 and the network attached to port 140 that alerts the owner of docking cart 14 or other suitable party that the cart is being used by an unauthorized user. This type of alarm-message arrangement may be used for any suitable equipment (e.g., other networked medical equipment) if desired.

The foregoing is merely illustrative of the principles of this invention and various modifications can be made by those skilled in the art without departing from the scope and spirit of the invention.

What is claimed is:

1. A docking cart to which a portable ultrasound unit is connected, the portable ultrasound unit (PUU) comprising a transducer port configured to be coupled to a connector of an ultrasound transducer and PUU ultrasound processing circuitry that accepts first ultrasound image data from the transducer port and processes the first ultrasound image data to generate second ultrasound image data, the docking cart comprising:

digital communications circuitry that supports communications between the docking cart and the connected portable ultrasound unit; and docking cart ultrasound processing circuitry that processes the second ultrasound image data received by the docking cart from the portable ultrasound unit through the digital communications circuitry, wherein the docking cart ultrasound processing circuitry is integrally disposed within the docking cart.

2. The docking cart defined in claim 1 further comprising an internal battery for powering the digital communications circuitry and docking cart ultrasound processing circuitry.

3. The docking cart defined in claim 1 further comprising at least one set of slider controls for making ultrasound gain-depth-compensation adjustments.

4. The docking cart defined in claim 1 further comprising a clinician display that displays ultrasound images gathered using the portable ultrasound unit.

5. The docking cart defined in claim 1 further comprising at least one transducer expansion port through which ultrasound image data from an ultrasound transducer is provided by the docking cart to the portable ultrasound unit.

6. The docking cart defined in claim 1 wherein the second ultrasound image data received by the docking cart from the portable ultrasound unit comprises digital channel data, the docking cart further comprising a display, wherein the communications circuitry and ultrasound processing circuitry of the docking cart are configured to:
   process the digital channel data; and
   display a resulting ultrasound image on the display.

7. The docking cart defined in claim 1 wherein the PUU processing circuitry generates the second ultrasound image data in the form of at least two different types of ultrasound image data selected from the group consisting of: channel data, RF data, detected data, scan-converted data, and formatted image data, the docking cart further comprising a display, wherein the communications circuitry and ultrasound processing circuitry of the docking cart are configured to display an ultrasound image on the display that is formed from at least one of the two different types of ultrasound image data.

8. The docking cart defined in claim 1 further comprising a display, wherein the second ultrasound image data generated by the PUU ultrasound processing circuitry includes third and fourth ultrasound image data, wherein the PUU ultrasound processing circuitry processes the third ultrasound image data to generate the fourth ultrasound image data, and wherein the docking cart communications circuitry and docking cart ultrasound processing circuitry are configured to process the third ultrasound image data and the fourth ultrasound image data and are configured to display corresponding ultrasound images on the display.

9. The docking cart defined in claim 1 wherein the portable ultrasound unit comprises a portable ultrasound unit display that supports a first display format, wherein the docking cart comprises a docking cart display that supports a second display format, and wherein the first and second display formats are different.

10. The docking cart defined in claim 1 further comprising a user interface having user controls and a user-adjustable mount with which the position of the user interface relative to the cart is adjusted.

11. The docking cart defined in claim 1 further comprising a display on which ultrasound images from the portable ultrasound unit are displayed by the docking cart ultrasound processing circuitry, the docking cart further comprising a user-adjustable mount with which the position of the display relative to the cart is adjusted.

12. The docking cart defined in claim 1 further comprising wheels on the cart that allow the cart to be moved.

13. The docking cart defined in claim 1 further comprising:
   a clinician display that displays ultrasound images for a clinician; and
   a patient display separate from the clinician display that displays ultrasound images for a patient.

14. The docking cart defined in claim 1 further comprising:
   a clinician display that displays ultrasound images for a clinician; and
   a patient display separate from the clinician display that displays ultrasound images for a patient, wherein at least some ultrasound image information that is displayed on the clinician display is not displayed on the patient display to avoid disturbing the patient.

15. The docking cart defined in claim 1 further comprising internal digital storage for storing ultrasound image data.

16. The docking cart defined in claim 1 further comprising internal digital storage for storing ultrasound image data, wherein the digital communications circuitry and the docking cart ultrasound processing circuitry are configured to download the second ultrasound image data from the portable ultrasound unit into the digital storage.

17. The docking cart defined in claim 1 further comprising internal digital storage for storing ultrasound image data, wherein the digital communications circuitry, the docking cart ultrasound processing circuitry, and the digital storage are configured to:
   maintain a database of a patient's images in the internal digital storage;
   allow the second ultrasound image data to be downloaded from the portable ultrasound unit into the internal digital storage; and
   compare the downloaded ultrasound image data to the database of patient's images to detect trends in the patient's condition.

18. The docking cart defined in claim 1 further comprising a writable removable disk device for storing ultrasound image data.

19. The docking cart defined in claim 1 further comprising an ultrasound gel warmer.

20. The docking cart defined in claim 1 further comprising a battery charging system for charging batteries for the portable ultrasound unit.

21. The docking cart defined in claim 1 further comprising a touch screen user interface that is used to receive commands from a user.

22. The docking cart defined in claim 1 further comprising at least one physiological input port that receives physiological data from a physiological sensor.

23. The docking cart defined in claim 1 further comprising at least one physiological input port that receives cardiac data from a patient and provides the cardiac data to the docking cart ultrasound processing circuitry.

24. The docking cart defined in claim 1 further comprising at least one communications port for supporting communications between the docking cart ultrasound processing circuitry and an external device connected to the communications port.

25. The docking cart defined in claim 1 further comprising audio speakers coupled to the docking cart ultrasound processing circuitry.

26. The docking cart defined in claim 1 further comprising:
   wheels on the cart that allow the cart to be moved; and
   a locking mechanism that prevents the wheels from rotating.

27. The docking cart defined in claim 1 further comprising:
   swiveling wheels on the cart; and
   a locking mechanism that prevents at least some of the wheels from swiveling.

28. The docking cart defined in claim 1 wherein the docking cart ultrasound processing circuitry is configured to determine whether the docking cart has been moved to an unauthorized location.

29. The docking cart defined in claim 1 wherein the docking cart ultrasound processing circuitry is configured to disable at least some operations when the docking cart ultrasound processing circuitry determines that the cart has been moved to a new network environment.

30. The docking cart defined in claim 1 further comprising a communications port that supports wireless communications between the docking cart ultrasound processing circuitry and a network.

31. The docking cart defined in claim 1 further comprising a thermal regulator that prevents the connected portable ultrasound unit from overheating.

32. The docking cart defined in claim 1 further comprising a docking cart receptacle in which the portable ultrasound unit is located.

33. The docking cart defined in claim 1 further comprising a docking cart receptacle in which the portable ultrasound unit is located, wherein the docking cart receptacle is configured so as not to block the transducer port of the portable ultrasound unit.

34. The docking cart defined in claim 1 further comprising an ultrasound transducer head holder.

35. A docking cart to which a portable ultrasound unit is connected, the docking cart comprising:

digital communications circuitry that supports communications between the docking cart and the connected portable ultrasound unit; and a processor that processes ultrasound image data received by the docking cart from the portable ultrasound unit through the digital communications circuitry, wherein the processor is configured to determine whether the docking cart has been moved to an unauthorized location.

36. A docking cart to which a portable ultrasound unit is connected, the docking cart comprising:

digital communications circuitry that supports communications between the docking cart and the connected portable ultrasound unit; and a processor that processes ultrasound image data received by the docking cart from the portable ultrasound unit through the digital communications circuitry, wherein the processor is configured to disable at least some operations when the processor determines that the cart has been moved to a new network environment.

* * * * *